US010440017B2

(12) United States Patent
Ramaci

(10) Patent No.: US 10,440,017 B2
(45) Date of Patent: Oct. 8, 2019

(54) SECURE HEALTH DATA STORAGE AND TRANSACTION SYSTEM

(71) Applicant: Elements of Genius, Inc., Isle of Palms, SC (US)

(72) Inventor: Jonathan E. Ramaci, Isle of Palms, SC (US)

(73) Assignee: Elements of Genius, Inc., Mt. Pleasant, SC (US)

( * ) Notice: Subject to any disclaimer, the term of this patent is extended or adjusted under 35 U.S.C. 154(b) by 59 days.

(21) Appl. No.: 15/462,349

(22) Filed: Mar. 17, 2017

(65) Prior Publication Data

US 2017/0213050 A1 Jul. 27, 2017
US 2017/0344755 A9 Nov. 30, 2017

Related U.S. Application Data

(60) Provisional application No. 62/286,556, filed on Jan. 25, 2016, provisional application No. 62/450,825, filed on Jan. 26, 2017.

(51) Int. Cl.
*H04L 29/06* (2006.01)
*G06F 19/00* (2018.01)
*G06F 21/62* (2013.01)

(52) U.S. Cl.
CPC ...... *H04L 63/0861* (2013.01); *G06F 19/3456* (2013.01); *G06F 21/6218* (2013.01); *H04L 63/101* (2013.01)

(58) Field of Classification Search
CPC ........ G06F 21/60; G06F 15/173; G06F 19/00; G06F 19/3456; G06F 21/6218;
(Continued)

(56) References Cited

U.S. PATENT DOCUMENTS 7,424,437 B2 * 9/2008 Maus .................. A61B 5/0002
 705/2
7,454,002 B1 11/2008 Gardner et al.
(Continued)

OTHER PUBLICATIONS

AARP, Inc.—American Association of Retired Persons; "2016 Health Innovation Frontiers", Copyright 2016, 23 pgs.
(Continued)

*Primary Examiner* — Thanhnga B Truong
(74) *Attorney, Agent, or Firm* — Gregory Finch; Finch Paolino, LLC

(57) ABSTRACT

Embodiments of the invention are directed to a system, method, or computer program product for a transaction apparatus for secure data storage and consolidation of medication adherence, health and wellness data for easy implementation and utilization during a transaction. The transaction apparatus may be configured, in various embodiments, for receiving, storing, encrypting, decrypting, encoding, decoding, accessing, transferring, writing, and/or presenting transaction data including, but not limited to, health care data, medication adherence data, wellness data, location data, authentication data, identification data, access data, personal data, and/or other data associated with a user. As such, the transaction apparatus may receive data from a user and store the data. The user may then provide authorization to access the data. The user may then select the data to be copied to an output device associated with the apparatus. The output devices may include, but are not limited to, an E-ink display, mobile devices, and the like.

16 Claims, 5 Drawing Sheets

(58) Field of Classification Search
CPC ..... G07F 19/00; G06Q 20/00; H04L 63/0861; H04L 63/101; H04L 9/32; G01N 33/00; G05B 19/00
USPC .............. 726/26, 28; 235/379; 709/227, 225
See application file for complete search history.

(56) References Cited

U.S. PATENT DOCUMENTS

| | | | |
|---|---|---|---|
| 9,508,070 B2 * | 11/2016 | Grigg | .................... G06Q 30/016 |
| 2005/0148890 A1 | 7/2005 | Hastings | |
| 2008/0238666 A1 | 10/2008 | Loncar | |
| 2009/0048868 A1 | 2/2009 | Portnoy et al. | |
| 2009/0083544 A1 * | 3/2009 | Scholnick | ............... G06F 21/14 |
| | | | 713/186 |
| 2014/0058865 A1 | 2/2014 | Yang et al. | |
| 2014/0075431 A1 | 3/2014 | Kumar et al. | |
| 2014/0379910 A1 | 12/2014 | Saxena et al. | |
| 2015/0026814 A1 * | 1/2015 | Caskey | ............... G06F 21/6245 |
| | | | 726/26 |
| 2015/0317455 A1 | 11/2015 | Lehmann et al. | |
| 2015/0371000 A1 | 12/2015 | Pinsonneault | |
| 2016/0042623 A1 | 2/2016 | Riley et al. | |
| 2016/0048667 A1 | 2/2016 | Kao | |
| 2016/0140308 A1 | 5/2016 | Ramsdell et al. | |
| 2016/0161985 A1 | 6/2016 | Zhang | |
| 2016/0328529 A1 | 11/2016 | Kalb et al. | |
| 2016/0342767 A1 | 11/2016 | Narasimhan et al. | |
| 2017/0045954 A1 * | 2/2017 | Leoni | ..................... G02F 1/167 |
| 2017/0308897 A1 | 10/2017 | Ramaci | |

OTHER PUBLICATIONS census.gov—United States Census Bureau; "An Aging World: 2015", Issued Mar. 2016, 175 pgs.
nih.gov—National Institutes of Health; "World's older population grows dramatically", Mar. 28, 2016, 3 pgs.

* cited by examiner

SECURE HEALTH DATA STORAGE AND TRANSACTION SYSTEM

CROSS-REFERENCE TO RELATED APPLICATIONS

Applicant claims the benefit of U.S. Provisional Patent Application No. 62/286,556, filed Jan. 25, 2016, and to U.S. Provisional Patent Application No. 62/450,825, filed Jan. 26, 2017, the disclosures of both of the aforementioned applications being specifically incorporated herein by reference in their entireties.

BACKGROUND

Today, most individuals have several medications that must be taken by him/her on a daily basis. These medications may have varying times to be taken and various dosages to be taken at varying times during the day.

These regimes and schedules become cumbersome for an individual to adhere to and manage as there is a complex matrix involved in the medication adherence of the individuals. Therefore these regimes and schedules are typically created, stored and managed in a notebook, piece of paper or other similar type of informal system.

These various health care data, medication adherence data, wellness data, location data, authentication data, identification data, access data, personal data, and/or other data associated with a user are important to the individual that is carrying the item. However, rarely do individuals carrying these items secure them.

Therefore a need exists for a method and apparatus for the consolidation of the various health care data, medication adherence data, wellness data, location data, authentication data, identification data, access data, personal data, and/or other data associated with a user in a secure manner.

BRIEF SUMMARY

The following presents a simplified summary of all embodiments in order to provide a basic understanding of such embodiments. This summary is not an extensive overview of all contemplated embodiments, and is intended to neither identify key or critical elements of all embodiments nor delineate the scope of any or all embodiments. Its sole purpose is to present some concepts of all embodiments in a simplified form as a prelude to the more detailed description that is presented later.

Embodiments of the present invention address the above needs and/or achieve other advantages by providing apparatus (e.g., a system, computer program product, and/or other devices) and methods for secure data storage and the consolidation of health care and identification items for easy implementation and utilization during a transaction.

The transaction apparatus as described herein may be, in some embodiments, associated with a mobile device. In other embodiments, the transaction apparatus may be a standalone device such as a wearable mobile device. In yet other embodiments the transaction apparatus may be integrated into the mobile device. The transaction apparatus typically includes a processor and memory device. The transaction apparatus may be configured, in various embodiments, for receiving, storing, encrypting, decrypting, encoding, decoding, accessing, transferring, writing, and/or presenting transaction data including, but not limited to, health care data, medication adherence data, wellness data, location data, authentication data, identification data, access data, personal data, and/or other data associated with a user.

In some embodiments, the transaction apparatus may receive data by communication with a mobile device, by still photography or video capture, by accessing the Internet via a network, by communication with a biometric reader, by receiving manual input by a user, micro USB port, SIM cards, accessing a cloud, geo-fence, radio, communication with other transaction apparatus, and/or the like. In some embodiments, the data received by the transaction apparatus may be determined to be associated with the user of the transaction apparatus, such that only data associated with the user and/or associated of the user may be stored in the transaction apparatus. In this way, individuals may not be able to receive and store other individual's health care data, medication adherence data, wellness data, location data, authentication data, identification data, access data, personal data, and/or other data associated with a user information or the like without the other individual's knowledge. Communication with the mobile device may be through a direct hardwire connection or network connection such as a connection through a wireless network such as a cellular phone provider wireless data network, Wi-Fi, Bonjour, and/or the Internet, Near Field Communication (NFC) connection, Bluetooth® connection, Bluetooth® Lite connection, and/or the like.

In some embodiments, the data received may be stored within the transaction apparatus. In some embodiments, the data may be stored in the transaction apparatus such that a mobile device or other device associated with the transaction apparatus may not have access to the data stored within the transaction apparatus. In some embodiments, the data may be stored in the transaction apparatus such that a mobile device or other device associated with the transaction apparatus may have limited access to the data stored within the transaction apparatus. The data stored within the transaction apparatus may be encrypted such that unwanted attempts to access the data may be denied. Furthermore, the data stored within the transaction apparatus may be protected because the connector(s) of the transaction apparatus are utilized by the processor such that PIN assignments differ from standard PIN assignments and, therefore, a peripheral attempting connection with the connector(s) of the transaction apparatus may not receive power from the expected PIN, may not be able to transfer data over expected PINs, and/or may be able to decode and/or decrypt data that stored and/or accessed from the transaction apparatus.

In some embodiments, a user of the transaction apparatus may access the data stored within the transaction apparatus. Prior to allowing access to all of the health care data, medication adherence data, wellness data, location data, authentication data, identification data, access data, personal data, and/or other data associated with a user and/or other data that is stored within the transaction apparatus, the user may be required to present authorization data to the transaction apparatus to ensure the user is authorized to access the data. The authorization data may be presented by the user to the mobile device, the transaction apparatus or a peripheral device, or otherwise. The authorization data may include biometric data or combinations of biometric data, such as fingerprint data captured by scanning a user's finger, retinal or iris data captured by scanning a user's eye(s), voice recognition, gestures and patterns, etc., data corresponding to a user's PIN, shape or object recognition authorization, and the like. The authorization, if accepted, may allow a user to utilize the data stored within the transaction apparatus. However, in some embodiments, the data may only be utilized for specific tasks. For example, some and/or all of the data may not be communicated from transaction apparatus to the mobile device despite successful authorization of the user.

In some embodiments, the authentication for utilization of the data stored within the transaction apparatus may be unsuccessful. In this way, in some embodiments, the transaction apparatus may provide emergency contact information for the user, such that the person attempting to access the transaction apparatus and or mobile device of a user unsuccessfully may have the ability to communication with emergency contacts of the uses in case of an emergency. In other embodiments, the transaction apparatus may lock the transaction data stored within the transaction apparatus upon unsuccessful attempts to access the data. In yet other embodiments, the transaction apparatus may potentially erase the transaction data upon several unsuccessful access attempts.

The user may access and view portions of the data via his/her mobile device or other computing device display utilizing an application or other program associated with the transaction apparatus. In this way, certain information may be stored within the transaction apparatus and not communicated to a mobile device or the like.

Accessing and viewing a representation of the data stored within the transaction apparatus on a display allows a user to select the health care data, medication adherence data, wellness data, location data, authentication data, identification data, access data, personal data, and/or other data associated with a user that the user may wish to use during a transaction.

Once the user selects the data from the display, the mobile device may present the selection to the transaction apparatus. The transaction apparatus will determine what data is stored in association with the user's selection and transfer that data to an output device.

In some embodiments, the transaction apparatus may present the selected data via an output device associated with the transaction apparatus. In this way, the output device may receive all data stored in the transaction apparatus associated with the selected health care data, medication adherence data, wellness data, location data, authentication data, identification data, access data, personal data, and/or other data associated with a user. Output devices may include, but are not limited to, an E-ink display, wireless communications, micro-USB, Wi-Fi, geo-fence, communications with a cloud, television, radio, other displays devices, and/or the like. The transaction apparatus may then communicate some or all the data to an E-ink display or other display associated with the transaction apparatus.

Upon completion of a user utilizing the data for a transaction via an output device, the output device may be programmed to erase any or all data from its memory/magnetic strip/etc. and/or the transaction apparatus may time-out the output device if it is connected to the transaction apparatus. In this way, the data may be removed from the output device to prevent misuse of the data.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Figure 1:
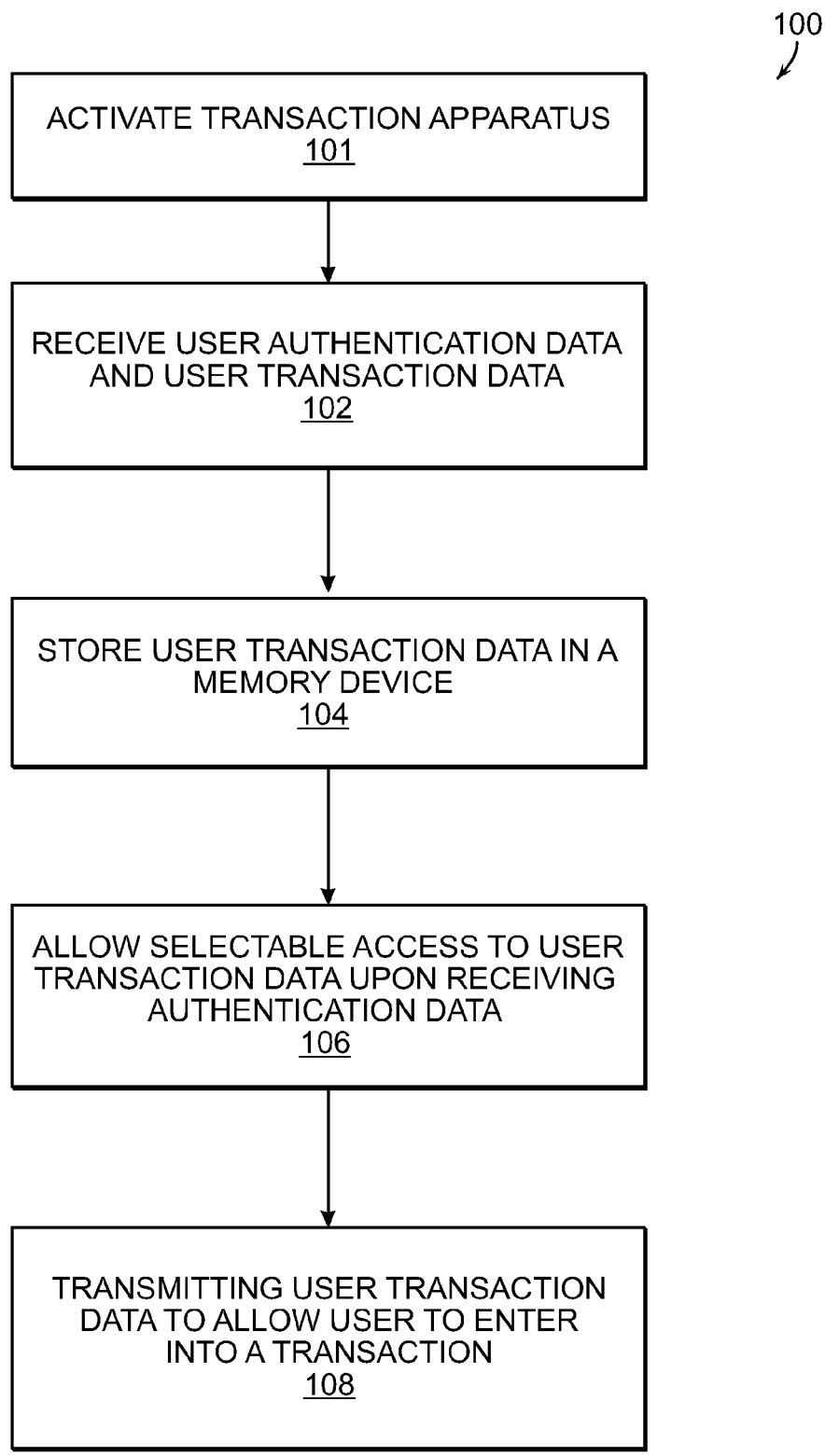
Figure 2:
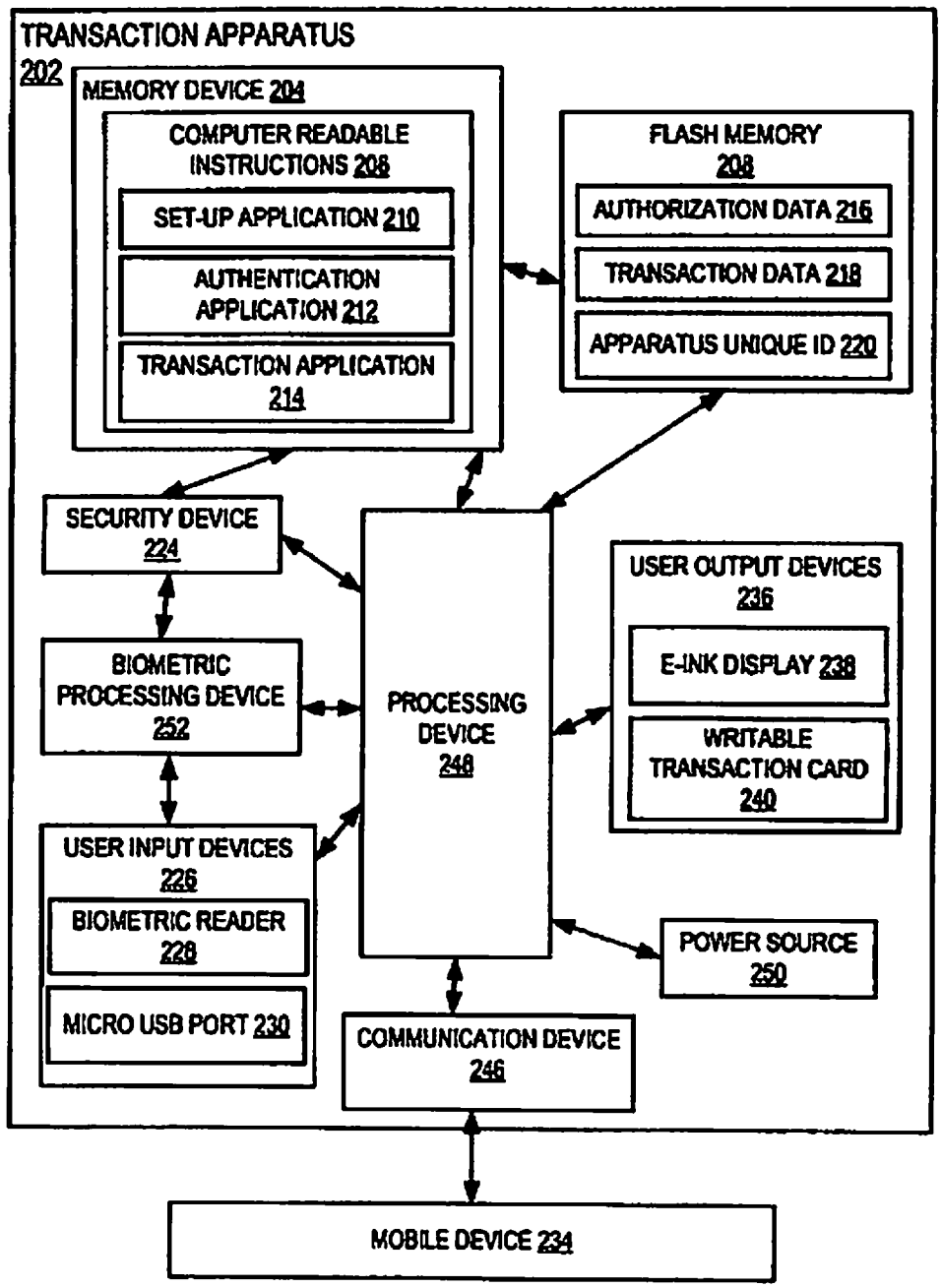
Figure 3:
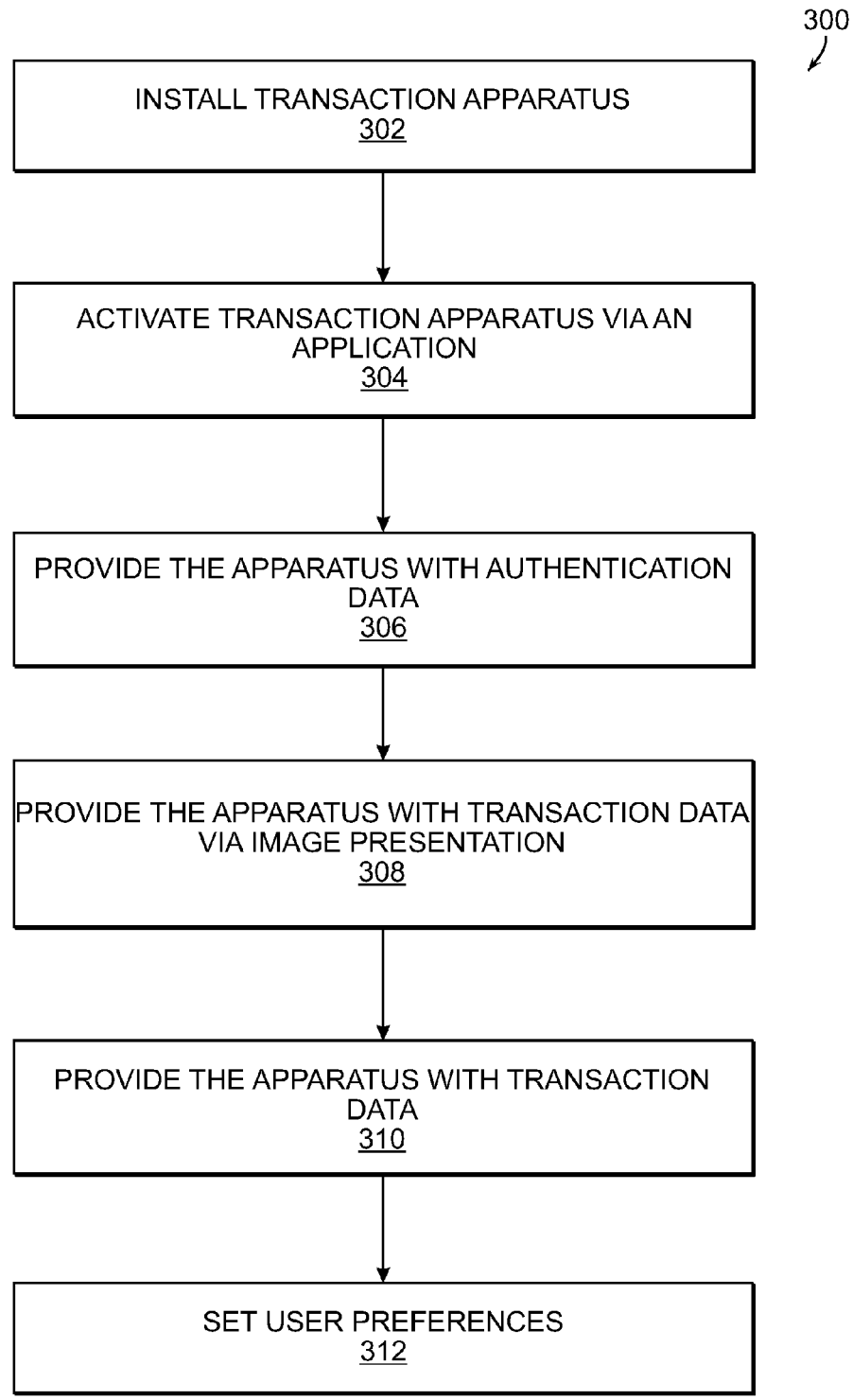
Figure 4:
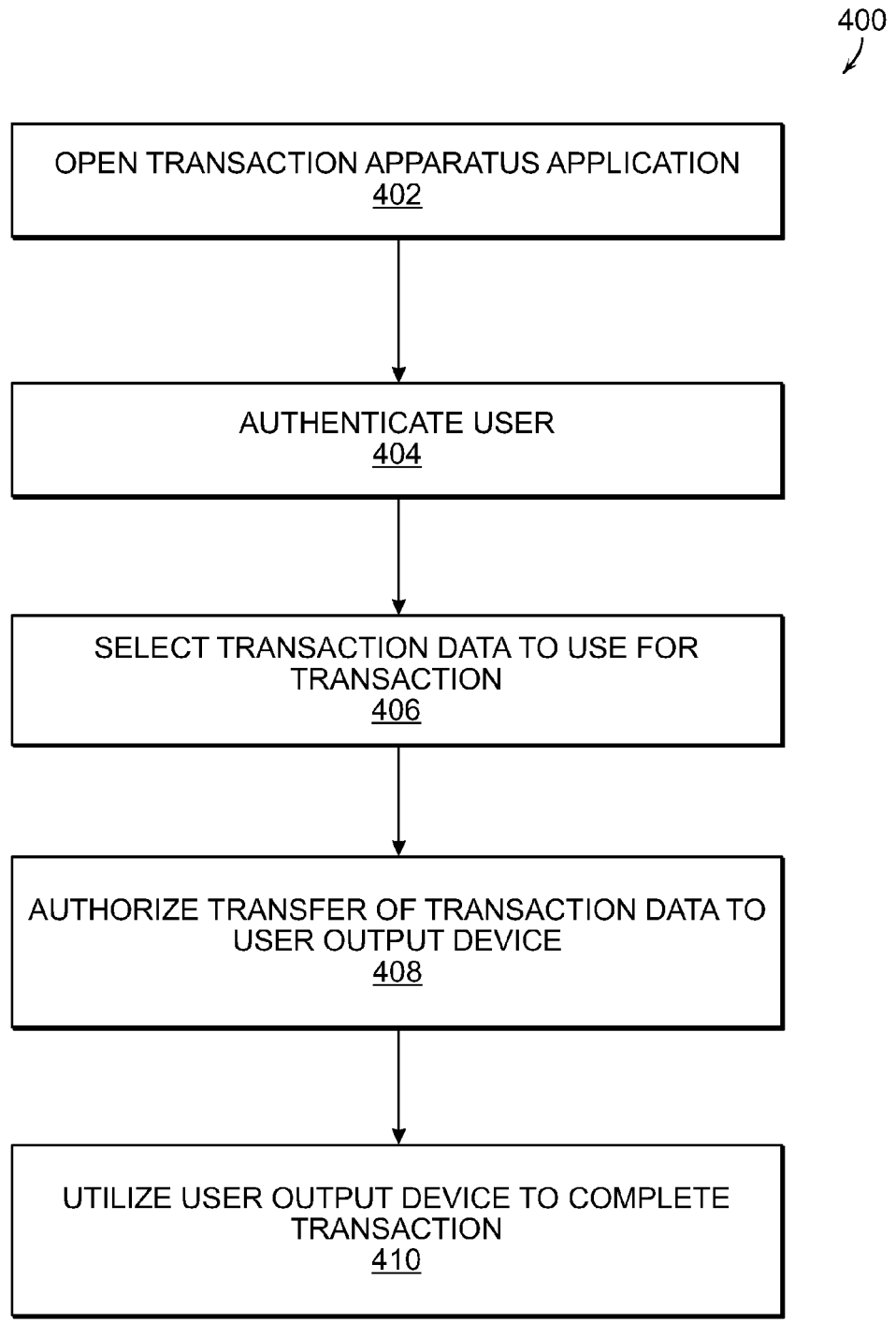
Figure 5:
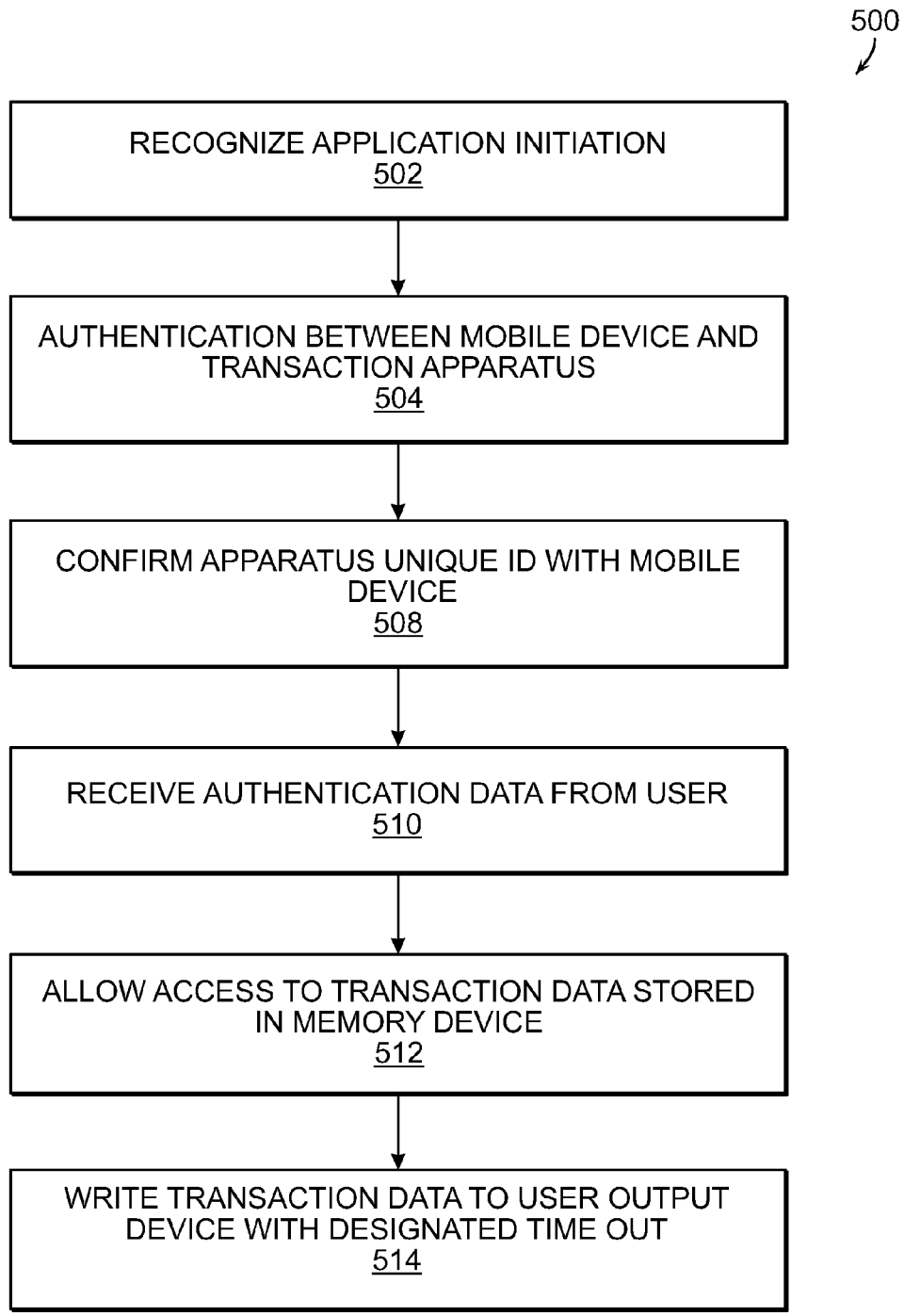

Having thus described embodiments of the invention in general terms, reference will now be made the accompanying drawings, wherein:

FIG. 1 provides a high level process flow illustrating the process of using transaction apparatus, in accordance with embodiments of the invention;

FIG. 2 provides an embodiment of the transaction apparatus computing system, in accordance with an embodiment of the invention;

FIG. 3 provides an illustration of a process flow for a user set-up of the transaction apparatus in accordance with an embodiment of the invention;

FIG. 4 provides an illustration of a process flow for user utilization of the transaction apparatus for entering into a transaction, in accordance with an embodiment of the invention; and FIG. 5 provides a process map illustrating the process flow for of the system wake-up and utilization for a transaction after a user has set-up the transaction apparatus, in accordance with an embodiment of the invention.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on." Like numbers refer to like elements throughout.

In accordance with embodiments of the invention, the term "transaction" as used herein may include any financial transaction, such as a health care information access; and/or other exchange of information from one party to another.

FIG. 1 illustrates a high level process flow of using the transaction apparatus 100. As illustrated in block 101 the transaction apparatus may be activated. Activating the transaction apparatus may, in some embodiments, include connecting the apparatus to a mobile device. In other embodiments, if the transaction apparatus is a standalone device, the device may simply need to be powered on via a battery, rechargeable cell, or the like. In other embodiments, opening an application associated with the transaction apparatus may activate the transaction apparatus. Once connected to a mobile device activation of the transaction apparatus may include downloading an application on his/her mobile device. The application may allow for a communication interface between the apparatus and the mobile device.

Next, as illustrated in block 102 the transaction apparatus may receive user authentication data and/or user transaction data. In some embodiments, the transaction apparatus may receive data by communication with a mobile device, photography, accessing the Internet via a network, biometric reader, manual input by a user, a Subscriber Identification Module (SIM) card, and the like. The communication with a mobile device may be through a direct hardwire connection, micro-Universal Serial Bus (USB) connection, Wi-Fi connection, cloud connections, Bonjour connection, Near Field Communication (NFC), Bluetooth®, Bluetooth® Lite, other network connections, etc. User authentication data may include unique user identifiers such as biometric scan data, such as finger print scanning, retinal scanning, etc, PINs, PIN authorization, shape or object recognition, passwords, and the like. User transaction data may include, but is not limited to health care data, medication adherence data, wellness data, location data, authentication data, identification data, access data, personal data, and/or other data associated with a user. Identification data may include insurance cards, identification cards, driver's license, social security cards, passports, business cards, etc. Health care data may include, but is not limited to medical records, prescriptions associated with a user, medical history, allergy information, etc.

As illustrated in block 104, the transaction apparatus may receive user authentication data and/or user transaction data. In some embodiments, the transaction apparatus may receive data by communication with a mobile device, photography, accessing the Internet via a network, biometric reader, manual input by a user, a Subscriber Identification Module (SIM) card, and the like. The communication with a mobile device may be through a direct hardwire connection, micro-Universal Serial Bus (USB) connection, Wi-Fi connection, cloud connections, Bonjour connection, Near Field Communication (NFC), Bluetooth®, Bluetooth® Lite, other network connections, etc. User authentication data may include unique user identifiers such as biometric scan data, such as finger print scanning, retinal scanning, etc, PINs, PIN authorization, shape or object recognition, passwords, and the like.

Next, as illustrated in 106 the transaction apparatus allows selectable access to the user transaction data. Prior to allowing selectable access to the user, the user may be required to present authorization data to the transaction apparatus to ensure the user is authorized to access the data. For example, the user may have provided authentication data in the form of a finger print scan in block 102. The user may now produce the same finger print scan in block 106 in order to allow the user access to the data. The authorization data may be presented by the user to the mobile device or the transaction apparatus. The authorization data may include data captured by biometric scanning, such as finger print scanning, retinal scanning, etc., PIN authorization, shape or object recognition authorization, and the like. The authorization, if accepted, may allow a user to utilize the data stored within the transaction apparatus. This provides security protection to a user's health care data, medication adherence data, wellness data, location data, authentication data, identification data, access data, personal data, and/or other data associated with a user, thus ensuring that the user is the only person able to access the data.

Finally, once the user selects the transaction data, the transaction apparatus may transmit the user transaction data to an output device such as an E-ink display, or biometric authentication device to allow the user to enter into a transaction, as illustrated in block 108. In this way, the output device may receive all data stored in the transaction apparatus associated with the selected transaction data and present the selected transaction data such that the user may utilize the transaction data to utilize for a transaction.

FIG. 2 illustrates an embodiment of the transaction apparatus computing system, in accordance with an embodiment of the invention. In some embodiments, when the transaction apparatus 202 is associated with a mobile device 234, the mobile device 234 is in communication with the transaction apparatus 202.

The mobile device 234 may be any communication device, including tablet devices, cellular telephones, personal digital assistant (PDA), a mobile Internet accessing device, or other user system including, but not limited to, pagers, televisions, gaming devices, laptop computers, desktop computers, cameras, video recorders, audio/video player, radio, GPS devices, any combination of the aforementioned, or the like. In some embodiments, a mobile device 234 includes a communication device, a processing device, and a memory device. The processing device is operatively coupled to the communication device and the memory device. The processing device uses the communication device to communicate with the transaction apparatus 202 and other devices. Furthermore, communication between the mobile device 234 and the transaction apparatus 202 may be commanded through the use of an application that may be operated by a user via a display associated with the mobile device 234.

The mobile device 234 may include computer-readable and executable instructions stored in the memory device, which in one embodiment may include computer-readable instructions structured as an application for causing the processor to initiate user viewing, user selection, and control of operations associated with the transaction apparatus. In some embodiments, the memory device includes data storage for storing data related to the mobile device including but not limited to data associated with the application for operating the transaction apparatus 202.

The transaction apparatus 202 generally comprises one or more processing devices. In some embodiments, only one processing device is necessary for the transaction apparatus 202. In yet other embodiments, two or more processing devices are necessary for the transaction apparatus 202. The transaction apparatus 202 illustrated in FIG. 2 has two processing devices: a transaction apparatus processing device 248 and a biometric processing device 252. The transaction apparatus 202 also includes one or more of memory device 204, flash memory 208, a security device 224, user input devices 226, user output devices 236, and optionally a power source 250.

The user input devices 226 allow a user to input transaction data and/or authorization data onto the flash memory 208 of the transaction apparatus 202. In some embodiments, a user input device 226 may include a biometric reader 228. The biometric reader 228, whether utilized for finger print providing, retinal scanning, and or the like may provide the flash memory 208 with authorization data 216 captured from a user desiring access to the transaction apparatus 202. In some embodiments, a user input device 226 may include a micro USB port 230. The micro USB port 230 allows the transaction apparatus 202 to be connected to a data reader device in order to receive data read from a user device such as a magnetic strip card data via a magnetic strip reader. In this way, the micro USB port 230 may provide the flash memory with transaction data 218. Furthermore, a user may utilize his/her mobile device 234 to input data to be stored in the flash memory 208. In some embodiments, user input devices 226 may include several other input devices or input connection capabilities, such as, but not limited to SIM cards, Wi-Fi connections, Bonjour connections, cloud connection, television connections, radio connections, connections, etc.

The flash memory 208 stores the authorization data 216, the transaction data 218, and the transaction apparatus unique ID 220. Authorization data 216 may include biometric scanning data, such as finger print scanning data, retinal scanning data, etc., PIN authorization, shape or object recognition authorization, and the like. Transaction data 218 may include health care data, medication adherence data, wellness data, location data, authentication data, identification data, access data, personal data, and/or other data associated with a user. In some embodiments the apparatus unique ID 220 is an identification that is unique to each individual transaction apparatus 202. In some embodiments, the apparatus unique ID 220 of the mobile device is compared to the apparatus unique ID 220 stored in the transaction apparatus 202 each time an application is opened by the mobile device that requests access to, or operation of, the transaction apparatus 202. In this way, a user may not be able to take another user's transaction apparatus, connect his/her mobile device such that he/she may be able to gain access to another individual's transaction data. In other embodiments, the apparatus unique ID 220 is confirmed when the mobile device is first connected with the transaction apparatus. In this way, the confirmation steps may only need to be performed once while the transaction apparatus and the mobile device remain connected. In other embodiments, the confirmation occurs based on a predetermined list of actions taken by the mobile device application, such as when the mobile device application requests access to generally inaccessible data. In some such embodiments, the transaction apparatus also confirm the identity of the user by biometric authentication or otherwise.

The power source 250 of the transaction apparatus 202 may be, in some embodiments, drawn from the mobile device 234. In some embodiments, the transaction apparatus 202 may comprise its own power source 250. In this way, the transaction apparatus may comprise a rechargeable battery or the like in order to power the system. In yet other embodiments, the power source 250 may include kinetic energy charging, solar power, wireless charging, wireless power, and/or the like.

The security device 224 communicates between the processing device 248, the biometric processing device 252, and the memory device 204. During the process of using the transaction apparatus 202 there are several security checks, such as a user authentication, apparatus unique ID, and/or the like. As such, at each check, if the authentication does not match correctly, the biometric processing device 252 may communicate with the security device 224 to provide a security feature to whomever is attempting to access the transaction apparatus 202. In some embodiments, the security device 224 may temporarily lock out the transaction data such that the attempted user may not be able to access the data if he/she (or the device) is not authenticated. In other embodiments, upon several failed authentication attempts the transaction apparatus 202 may present the authenticated user's emergency contact information. In this way, if the user and/or another individual whom is attempting to access the transaction apparatus 202 but is unsuccessful may receive emergency contact information to the attempted user. In yet other embodiments, the transaction apparatus 202 may erase the flash memory of the transaction apparatus 202. In this way, the security device 224 may completely erase the transaction data 218 such that other individuals may not be able to access the transaction data 218 of the user.

As illustrated, the transaction apparatus 202 comprises a general processing device 248 and a biometric processing device 252. As used herein, the term "processing device" generally includes circuitry used for implementing the communication and/or logic functions of the particular system. For example, a processing device may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. In some embodiments a processor may comprise one or more peripheral interface controllers associated therein. A processing device may include functionality to operate one or more software programs based on computer-readable instructions thereof, which may be stored in a memory device.

The biometric processing device 252 is associated with the user input devices 226 and the communication device 246 to determine if the user attempting to access the data on the transaction apparatus 202 is authorized to do so. The biometric processing device 252 provides for multiple authentication checks. The biometric processing device 252 may match the apparatus unique ID 220 between a mobile device and the transaction apparatus and the biometric processing device 252 may also match authorization data from a user input device 226 with authorization data 216 stored in the flash memory 202. These security features ensure that the user who is attempting to access the transaction data of a user. First, the biometric processing device 252 upon receiving an indication that the application associated with operating and user command for operating the transaction apparatus 202, will provide a security check for the apparatus unique ID 220 with the mobile device 234 operating system. In other words, the biometric processing device 252 compares the apparatus unique ID 220 corresponding to the mobile device 234 with the apparatus unique ID 220 stored in the transaction apparatus 202. Second, the biometric processing device may communicate with user input devices 226 to receive authentication data 216 from a user input device 226 such as a biometric reader 228. Upon receiving the authorization data from the user input device the biometric reader 228 may attempt to match the authorization data received to the authorization data 216 stored in the flash memory 208. If one of these authorization steps performed by the biometric processing device 252 does not match, the biometric processing device 252 communicates with the security device 224 to ensure the correct security feature is provided, such as locking out the data, providing emergency contact information, or erasing the data in the flash memory 208. If, however, the biometric processing device 252 determines that authentication has been matched, the system may allow the user to continue the process of accessing the user transaction data to present to an output device 236.

The processing device 248 is operatively coupled to the communication device, the memory device 204, flash memory 208, the biometric processing device 252, user input devices 226, and user output devices 236. The processing device 248 uses the communication device 246 to communicate with a mobile device 234. As such, the communication device 246 generally comprises a modem, server, or other device for communicating with the mobile device 234 and other devices.

The communication device allows for communication between the transaction apparatus 202 and a mobile device 234. In some embodiments this communication may be a direct hardwire connection between the transaction apparatus 202 and the mobile device 234. In other embodiments, the communication may be via network connection such as through NFC, Wi-Fi, Bluetooth®, Bluetooth® Lite, cloud communication, radio, and/or the like. When an application that communicates with the transaction apparatus 202 is opened on the user's mobile device 234 an operating system session is opened. Prior to any utilization of the transaction apparatus 202 when it is associated with a mobile device 234, there is an authentication between a processor associated with the mobile device 234 and the transaction apparatus 202. Once this authentication has been completed the transaction apparatus 202 using the communication device 246 is able to communicate with the mobile device 234 using the mobile device 234 operating system protocol.

As further illustrated in FIG. 2 the transaction apparatus comprises user output devices 236. These user output devices 236 are utilized to present transaction data to a second party. The output devices 236 include an E-ink display 238, wireless communication, hardwire communication, Wi-Fi, NFC, geo-fence, micro-USB port, Bonjour networks, cloud communication, television, radio, etc.

The E-ink display 238 may present 10 bar code, 20 bar code such as a QR code, coupon, identification information, advertisements, skew numbers, micro-bulletin boards, the unique transaction apparatus ID 220, color data, mobile device data, such as, but not limited to data lists, text messages, reminders, and/or the like on the transaction apparatus 202. In this way, the user may be able to present transaction data on the E-ink display 238 in preparation for or during a transaction. The standard bar code scanner may not be able to recognize bar codes that are produced on a backlit screen, such as those found in most cellular phones, tablet computers, lap top computers, and the like. Accordingly, if a loyalty card is reproduced on one of these backlit screens, the point of sale bar code scanner will not be able to read the bar code effectively. The transaction apparatus 202 may provide the user with an E-ink display 238 that provides a dull ink like finish to a separate display associated with the transaction apparatus 202. Therefore a typical bar code scanner may be able to scan the E-ink display in order to scan the information associated with transaction data that is in a form scan-friendly form.

As further illustrated in FIG. 2, the transaction apparatus 202 comprises computer-readable instructions 206 stored in a memory device 204, which in one embodiment includes the computer-readable instructions 206 of a set-up application 210, an authentication application 212, and a transaction application 214. In some embodiments, the memory device 206 includes data storage for storing data related to the set-up application 210, an authentication application 212, and a transaction application 214.

In some embodiments, as described in more detail below in FIG. 3, the set-up application 210 allows for initiation and set up of the transaction apparatus 202 as well as the input of data into flash memory 208. The set-up application 210 allows for set-up of the transaction apparatus 202 including the receiving of transaction data and authorization data as well as the storing of the same.

In some embodiments, as described in more detail below in FIG. 4, the authentication application 212 authenticates the mobile device 234 communication with the transaction apparatus 202 and authenticates the user for use of the transaction apparatus 202.

In some embodiments, as described in more detail below in FIG. 5, the transaction application 214 allows for user access to a limited amount of transaction data, user selection of the transaction data for use during a transaction, the transferring of transaction data to an output device 236, and/or in some embodiments, the presentment of transaction data on the output device 236.

It is understood that the servers, systems, and devices described herein illustrate one embodiment of the invention. It is further understood that one or more of the servers, systems, and devices can be combined in other embodiments and still function in the same or similar way as the embodiments described herein. Furthermore, one or more of the components, devices, systems, etc. discussed herein may be optional and may not be included in various embodiments of the invention.

FIG. 3 illustrates a process flow for a user set-up of the transaction apparatus 300, in accordance with an embodiment of the invention. As illustrated in block 302, the transaction apparatus may be installed. In some embodiments, the transaction apparatus may be associated with a mobile device. In other embodiments, the transaction apparatus may be a standalone device. In some embodiments of the invention, the installation of the transaction apparatus may require a hardwire or wireless connection to a mobile device.

Next, as illustrated in block 306, the user may provide the transaction apparatus with authentication data. Authorization data may include but is not limited to biometric data, such as fingerprint data captured by scanning a user's finger, retinal data captured by scanning a user's eye(s), etc., data corresponding to a user's PIN, shape or object recognition authorization, and/or any other data that may be unique to the user.

The user may upon activation of the transaction apparatus in block 304 provide the transaction apparatus with authentication data in several ways. The user may provide the transaction apparatus with authentication data utilizing communications with a mobile device by still photography or video capture, Internet access via a network, a biometric reader, by receiving manual input by a user, micro USB port, SIM card access, accessing a cloud, geo-fence, radio, communication with other transaction apparatus, and/or the like.

In some embodiments, the application may prompt the user to provide specific authentication data. In other embodiments, the user may select which authentication data to provide.

In some embodiments, the user may also provide transaction data. In some embodiments, the user may provide transaction data simultaneously with authentication data. In some embodiments, the user may provide transaction data prior to providing the authentication data. In yet other embodiments, the user may provide transaction data after providing the authentication data. In some embodiments, the user may provide transaction data in several ways, including the ways the user presents authentication data, as described above. These ways may include, but are not limited to utilizing communications with a mobile device by image presentation (such as still photography or video capture), Internet access via a network, manual input, a biometric reader, by receiving manual input by a user, micro USB port, SIM card access, accessing a cloud, pulling data, inferred, geo-fence, radio, communication with other transaction apparatus, and/or the like.

In some embodiments, the transaction data provided to the transaction apparatus may be determined, by the transaction apparatus, to be associated with the user of the transaction apparatus. In this way, based on the authentication data, the transaction data received at the transaction apparatus may only be associated with the user and/or user associates. Thus, transaction data not associated with the user of the transaction apparatus may not be stored in the transaction apparatus. As such, an individual may not be able store another individual's transaction data without his/her permission.

As illustrated in block 308, the apparatus may be provided with transaction data via image presentation. Image presentation may be done by still photography, video capture, inferred, laser reading, scanning, Internet communication, and/or the like. Utilizing still photography or video capture the transaction apparatus may capture and decode data associated with a ID, 2D, or 3D barcode, healthcare document, coupon, identification document, and/or the like. Capturing the still photography or video may, in some embodiments, be performed by the transaction apparatus. In some embodiments, the still photography or video may be captured by the mobile device. In other embodiments, the still photography or video may be captured by another device that is associated with the transaction apparatus. The transaction apparatus may also be able to decode data associated with QR codes, prescriptions, images on cards, identification cards, healthcare data, x-rays, etc.

Next, as illustrated in block 312, the user is able to set preferences within the application for the utilization of data by the transaction apparatus using an output device associated with the same. Preferences may include, but are not limited to the user being able to time-in and/or time-out the data on an output device. In this way, when the data is transmitted from the transaction apparatus to an output device. The data may only exist on the output device for a specific amount of time before the data is erased from the output device. Preferences may also include, but are not limited to application design preferences, data access preferences, data organization preferences, and/or the like.

FIG. 4 illustrates a process flow for user utilization of the transaction apparatus for entering into a transaction 400, in accordance with an embodiment of the invention. As illustrated in block 402 the user may open the transaction apparatus application. The application may be associated with a mobile device and/or the transaction apparatus. The application may then communicate with the transaction apparatus to initiate a session with the transaction apparatus. Whether the session is for receiving, storing, encrypting, decrypting, encoding, decoding, accessing, transferring, writing, and/or presenting transaction data using the transaction apparatus, the session may be initiated by the user opening the application.

The user may then, as illustrated in block 404, be authenticated. In some embodiments, the user may provide authentication via a biometric reader associated with the transaction apparatus. As such, the user may swipe his/her finger on a biometric reader associated with the transaction apparatus in order to be authenticated. The finger print scan of a user may match previously provided authentication data that the transaction apparatus received. If the authentication is a match, the application presents the user with options for selecting transaction data to use for a transaction, as represented by block 406. However, if the user authentication is not a match to the authentication data previously presented to the transaction apparatus, the transaction apparatus, via the application, may provide emergency contacts for the user, lock out the user, or erase the transaction data stored within the transaction device.

As illustrated in block 406, the user, using the application, may select the transaction data he/she wishes to use for a transaction. The data may be transferred to one or more output devices, such as an E-ink reader, Wi-Fi, Bluetooth, Bluetooth Lite, etc. The transfer of transaction data may also include time-out data, such that the data may be erased from an output device after a predetermined amount of time.

Finally, as illustrated in block 410 the user may utilize the output device to complete the transaction. For example, the user may be able to present identification, medication, prescriptions, a loyalty card, and/or the like via the E-ink display.

FIG. 5 illustrates a method 500 for the process of the system wake-up and utilization for a transaction after a user has set-up the transaction apparatus, in accordance with an embodiment of the invention. The transaction apparatus may wake-up upon recognition of application initiation 502. As described in further detail above, the user may activate an application that may communicate with and provide commands to the transaction apparatus and the transaction apparatus system therein. The activation of the application initiates an Operating System (OS) session.

Once the OS session has been initiated a chip associated with the mobile device may communicate with the transaction apparatus. This communication may, as illustrated in block 504, be an authentication between the mobile device and the transaction apparatus to ensure connection and that the user wishes to utilize the transaction apparatus for a transaction.

Next, as illustrated in block 506, once the mobile device and the transaction apparatus have authenticated, there is an adjustment of the amount of current being directed to the transaction apparatus. In some embodiments, the source of this current may be the transaction apparatus itself. In other embodiments, the source for this current may be a mobile device associated with the transaction apparatus. In yet other embodiments, the transaction apparatus may draw current from a wireless network or the like.

Block 508 of FIG. 5 illustrates that a confirmation of the transaction apparatus unique ID with the mobile device may occur next, after power to the transaction apparatus has been adjusted. In some embodiments, the authentication at this point may be a quick communication of the transaction apparatus unique ID. This authorization process may occur quickly, within seconds or fractions of a second, without user knowledge of the authentication. This authentication is to ensure that the user has used the currently associated mobile device in conjunction with the transaction apparatus in the past. For example, if an individual attempts to steal a user's transaction apparatus and attempts to activate it using his/her own mobile device (in order to obtain transaction data from the user) the apparatus unique IDs of the transaction apparatus and the mobile device will not match. Accordingly, the individual will not be able to gain access to the user's transaction data.

Once the apparatus unique ID has been confirmed as illustrated in block 508, the user may be prompted to provide authentication data of the user. This authentication data may be in many forms, including, but not limited to biometric readers, such as finger prints, PINs, shape matching, passwords, passcodes, etc. The transaction apparatus may then receive the authentication data from the user, as illustrated in block 510. Once received, the transaction apparatus may compare the received authentication data to authentication data previously received and stored in the transaction apparatus. For example, a user may have previously stored finger print data as his/her authentication data. The finger print data may have been scanned via a biometric reader on the transaction apparatus and stored within the transaction apparatus. As such, when the user is attempting to utilize the transaction apparatus, he/she may present the same finger to the biometric scanner. If no match is determined, in some embodiments, the transaction apparatus, through the application may present emergency contacts for the user. In some embodiments, the transaction apparatus may lock the user out of the transaction apparatus such that he/she may not be able to access some or all the transaction data stored on the transaction apparatus. In yet other embodiments, the transaction apparatus may erase the data stored on the transaction apparatus upon failure of authentication.

If the transaction apparatus indicates that a match exists between the finger print of the user and the finger print previously stored, the user is authorized access to the entire application and the data stored on the transaction device as illustrated in block 512. At this point, a portion of the transaction data is allowed to be accessed and viewed by a user via his/her mobile device display utilizing the application or another program associated with the transaction apparatus. In some embodiments, only a portion of the transaction data is viewable by the user.

The user may then select the output device to transfer the transaction data to. The transaction apparatus may then write to the user output device based on user preferences, as illustrated in block 514. The transaction apparatus may write data to an output device including an E-ink display, wireless communication, etc. In some embodiments, the transaction data may be written to an E-ink display. The E-ink display may receive transaction data from the transaction apparatus formatted to fit on the E-ink display and be potentially used for a transaction. The E-ink display may display in color E-ink, grey scale E-ink, or the like. The E-ink may be used to display any data the user may request. As such, the user may utilize the E-ink display for not only transaction data, but any other data, communications, and/or functions of a mobile device and/or the transaction apparatus.

The transaction apparatus, in this embodiment, comprises a biometric reader 18 for user input and authorization. In some embodiments, the biometric reader may be integrated into the mobile device. In other embodiments, no biometric reader may be associated with the transaction apparatus or mobile device. Furthermore, the transaction apparatus may also include an aperture 22 for connection of user input and/or output devices.

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language such as Java, Perl, Smalltalk, C++, or the like. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s).

The computer-executable program code may also be loaded onto a computer or other programmable data processing apparatus to cause a series of operational phases to be performed on the computer or other programmable apparatus to produce a computer-implemented process such that the code portions which execute on the computer or other programmable apparatus provide phases for implementing the functions/acts specified in the flowchart and/or block diagram block(s). Alternatively, computer program implemented phases or acts may be combined with operator or human implemented phases or acts in order to carry out an embodiment of the invention.

As the phrase is used herein, a processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

Embodiments of the present invention are described above with reference to flowcharts and/or block diagrams. It will be understood that phases of the processes described herein may be performed in orders different than those illustrated in the flowcharts. In other words, the processes represented by the blocks of a flowchart may, in some embodiments, be in performed in an order other that the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A system comprising:
   a transaction apparatus, the transaction apparatus comprising:
      a memory device; and
      a processing device operatively coupled to the memory device; and
   an output device associated with the transaction apparatus and being operatively coupled to the memory device, the output device being selected from the group consisting of an E-ink display, a micro-USB, a Wi-Fi device and a cloud-based communications device,
      wherein the processing device of the transaction apparatus is configured to execute computer-readable program code of the system to:
         receive one or more authorization provisions, the one or more authorization provisions comprising biometric scan data of a user;
         store the one or more authorization provisions in the memory device;
         authenticate the user according to the one or more authorization provisions stored in the memory device;
         receive a plurality of transaction data associated with the authenticated user, the plurality of transaction data comprising health and personal data of the authenticated user;
         store the plurality of transaction data in the memory device;
         configure preferences set by the authenticated user for utilization of the transaction data stored in the memory device by and between the transaction apparatus and the output device;
         display, via a display, a representation of the transaction data stored in the transaction apparatus for selection by the authenticated user;
         receive a transaction request by the authenticated user; and
         communicate at least a portion of the plurality of transaction data associated with the transaction request to the output device based on the preferences set by the authenticated user.

2. The system of claim 1 further comprising a mobile device communicably engaged with the transaction apparatus, the mobile device comprising:
   a mobile communication device;
   a mobile memory device; and
   a mobile processing device operatively coupled to the mobile communication device and the mobile memory device,
      wherein the mobile processing device is configured to execute computer-readable instructions stored in the mobile memory device to command communication between the mobile device and the transaction apparatus.

3. The system of claim 2 wherein the mobile device is configured to communicate the transaction data selected by the authenticated user to the transaction apparatus in response to the selection made by the authenticated user from the representation of the transaction data stored in the transaction apparatus on the display.

4. The system of claim 2 wherein the mobile device is configured to receive the biometric scan data from the user, and to communicate the biometric scan data of the user to the transaction apparatus.

5. The system of claim 2 wherein the mobile device is configured to display the transaction data associated with the transaction request by the authenticated user in response to the transaction request by the authenticated user.

6. The system of claim 2 wherein the mobile device has limited access to the transaction data stored in the transaction apparatus.

7. The system of claim 1 wherein the output device is programmed to erase the transaction data communicated to the output device by the transaction apparatus in response to the transaction request by the authenticated user upon completion of the authenticated user utilizing the data for the transaction.

8. The system of claim 1, wherein the transaction apparatus further comprises a biometric processing device.

9. The system of claim 1 wherein the biometric scan data is at least one selected from the group consisting of finger print scan, retinal scan, and facial scan.

10. The system of claim 1 wherein the output device is an E-ink display and the transaction data is displayed as a bar code.

11. A computer program product comprising at least one non-transitory computer-readable medium having computer-readable program code portions embodied therein, the computer-readable program code portions comprising:
   an executable portion configured for establishing one or more authorization provisions, the one or more authorization provisions comprising biometric scan data of a user of the computer program product;
   an executable portion configured for storing the one or more authorization provisions in a memory device of the computer program product;

an executable portion configured for authenticating the user according to the one or more authorization provisions stored in the memory device;

an executable portion configured for receiving a plurality of transaction data associated with the authenticated user, the plurality of transaction data comprising health and personal data of the authenticated user;

an executable portion configured for storing the plurality of transaction data in the memory device;

an executable portion configured for establishing preferences set by the authenticated user for utilization of the transaction data stored in the memory device by and between the computer program product and an output device;

an executable portion configured for displaying, via a display, a representation of the transaction data stored in the memory device for selection by the authenticated user;

an executable portion configured for receiving a transaction request by the authenticated user; and an executable portion configured for communicating at least a portion of the plurality of transaction data associated with the transaction request to the output device based on the preferences set by the authenticated user.

12. The computer program product of claim 11 further comprising an executable portion configured for establishing a unique device association between the computer program product and a mobile device.

13. The computer program product of claim 11 further comprising an executable portion configured for encrypting the plurality of transaction data prior to storing the plurality of transaction data in the memory device.

14. The computer program product of claim 12 further comprising an executable portion configured for receiving the biometric scan data of the user from the mobile device for authenticating the user according to the one or more authorization provisions.

15. The computer program product of claim 14 wherein the biometric scan data is at least one selected from the group consisting of finger print scan, retinal scan, and facial scan.

16. The computer program product of claim 11 wherein the output device is an E-ink display and the transaction data is displayed as a bar code.

* * * * *